United States Patent [19]
Baumbach et al.

[11] Patent Number: 4,539,994
[45] Date of Patent: Sep. 10, 1985

[54] METHOD FOR TRANSCUTANEOUS MEASUREMENT OF A BLOOD PARAMETER AND AN ELECTROCHEMICAL MEASURING ELECTRODE DEVICE FOR CARRYING OUT THE METHOD

[75] Inventors: Per L. Baumbach, Copenhagen; Jorgen Poulsen, Århus, both of Denmark

[73] Assignee: Radiometer A/S, Copenhagen, Denmark

[21] Appl. No.: 509,441
[22] PCT Filed: Oct. 12, 1982
[86] PCT No.: PCT/DK82/00093
§ 371 Date: Jun. 6, 1983
§ 102(e) Date: Jun. 6, 1983
[87] PCT Pub. No.: WO83/01510
PCT Pub. Date: Apr. 28, 1983

[30] Foreign Application Priority Data
Oct. 13, 1981 [DK] Denmark .............................. 4546/81

[51] Int. Cl.³ .............................................. A61B 5/00
[52] U.S. Cl. ..................................... 128/635; 204/403; 204/408
[58] Field of Search ................. 128/635; 204/403, 408, 204/415, 431, 433

[56] References Cited
U.S. PATENT DOCUMENTS
3,518,179  6/1970  Bleak et al. .......................... 204/408
4,311,151  1/1982  Hagihara ............................. 128/635
4,324,256  4/1982  Vesterager .......................... 128/635

FOREIGN PATENT DOCUMENTS
0143246   8/1981  Denmark .
10136     4/1980  European Pat. Off. .
2628288  12/1977  Fed. Rep. of Germany .
2758413   7/1978  Fed. Rep. of Germany .
2906201   8/1979  Fed. Rep. of Germany .
0130779  10/1974  Norway .
WO80/02795 12/1980 PCT Int'l Appl. .
2020819  11/1979  United Kingdom .

OTHER PUBLICATIONS
Hebrank, D. R., Journal of Clinical Engineering, vol. 6, No. 1, pp. 41–47, Jan.–Mar. 1981.
Thunstrom, A. M., et al., Birth Defects, Original Articles Series, vol. XV, No. 4, pp. 167–182, 1979.
Beran, A. V., Critical Care Medicine, vol. 9, No. 10, pp. 736–741, Oct. 1981.

Primary Examiner—Lee S. Cohen
Attorney, Agent, or Firm—Stiefel, Gross, Kurland & Pavane

[57] ABSTRACT

In accordance with the principles for transcutaneous measurement of a blood parameter, such as the partial pressure of a blood gas, an electrochemical measuring electrode device (1) is applied to the skin surface (2) of a person. The electrode device has a body (10), e.g. a thick film substrate, which is thermostated to a predetermined temperature and, furthermore, includes a sensor (11) together with a membrane (14) confining an electrolyte solution within an electrolyte reservoir (15). Furthermore, the electrode device includes a jacket having an annular metallic body (16), a metallic body (4) and a thick film substrate (8), which is thermostated to the same temperature as the body (10) of the electrode device. When the body is brought into contact with the skin surface, an annular surface part of the jacket is also brought into contact with the skin surface so that a virtual heating jacket is established in the skin beneath the annular surface part so as to substantially direct all heat flow from the body to tissue directly beneath the skin surface. By measuring the power supplied for thermostating the body to the predetermined temperature, the local capillary blood flow in the tissue (2) beneath the skin is measured, and the blood parameter in question is measured by means of the sensor (11). In an alternative operational mode, the electrode device is adapted to measure deep body temperature by thermostating the jacket to a temperature so that the temperature registered by a temperature sensor of the body and the temperature registered by a temperature sensor of the jacket are identical to one another and, consequently, identical to the deep body temperature.

28 Claims, 12 Drawing Figures

METHOD FOR TRANSCUTANEOUS MEASUREMENT OF A BLOOD PARAMETER AND AN ELECTROCHEMICAL MEASURING ELECTRODE DEVICE FOR CARRYING OUT THE METHOD

BACKGROUND OF THE INVENTION

The present invention relates to electrochemical measuring electrode devices for transcutaneous measurement of a blood parameter, such as the partial pressure of a blood gas. The transcutaneous measuring technique is well-known in the art. In accordance with the transcutaneous measuring technique, an electrode device for measuring the blood parameter in question is applied to a skin surface of a person in whom the blood parameter is to be measured. The electrode device is thermostated to a predetermined temperature, normally (when the blood parameter to be measured is, e.g., the partial pressure of a blood gas such as oxygen) a temperature above normal skin temperature so as to cause local hyperaemia in the skin surface in contact with the electrode.

Above certain minimum levels of perfusion in the skin area where the transcutaneous measurement is performed, parameters measured transcutaneously, e.g. blood gas partial pressures, reflect the corresponding arterial values which are the values normally used for clinical purposes. Below such minimum levels, the parameters measured transcutaneously can no longer be considered as reflecting the arterial values.

For this reason, it is important to monitor the local capillary blood flow concomittantly with the local transcutaneous measurement of a blood parameter. Furthermore, calculation methods have been suggested which convert the transcutaneously measured values into calculated values correlating to a higher degree with actual arterial values when, in addition to the perfusion, the metabolic oxygen consumption, the capillary temperature, and the skin diffusion gradient are also known or estimated.

It has been suggested, cf. e.g. Journal of Clinical Engineering, 6, No. 1, January/March 1981, pp 41–47 (Reference 1), Birth Defects, Original Article Series Vol. XV, No. 4, pp 167–182, 1979 (Reference 2), and Critical Care Medicine, October 1981, Vol. 9, No. 10, pp 736–741 (reference 3) to monitor the local capillary blood flow by measuring the power supplied to the transcutaneous electrochemical measuring devices to keep the devices at a constant temperature.

However, according to Reference 1, merely about 10–15% of the total sensor power is perfusion-dependent. Reference 2 suggests a device where the heat exchange with the surroundings is limited by means of a heat shell over the electrode device, the heat shell being circulated with water at electrode temperature, but reports that only about 30% of the heat transferred from the electrode to the skin is flow related. Reference 3 suggests a combined $O_2/CO_2$ and flow sensor which is adapted to be mounted on the forearm of a test person. Apart from a first servo-controlled heater/thermistor arranged in heat-conductive contact with a first heater assembly and serving the above described purpose of causing local hyperemia in the skin surface in contact with the sensor, a second servo-controlled heater/thermistor is included and arranged in heat-conductive contact with a second heater assembly arranged on the outside of the sensor. The second servo-controlled heater/thermistor is adapted to maintain the temperature of the second heater assembly at a temperature of 0.5° C. below the temperature of the first heater assembly. Thus, the second heater assembly which is not contacted with the skin surface merely serves thermal insulation purposes. When employed in conjunction with an occlusive system which is adapted to be arranged enclosing the entire forearm of a test person or patient and, furthermore, increases the insulation properties, the sensor is reported to be able to register a perfusion-dependent heat transfer to the skin of approximately 50% of the total sensor power.

SUMMARY OF THE INVENTION

The invention provides an electrochemical measuring electrode device for transcutaneous measurement of a blood parameter, said device comprising, in combination:

a body of a heat-conductive material having a surface part adapted to be applied to a skin surface in heat-conductive relationship therewith, said body including sensor means adapted to respond, in operation, to said blood parameter, and first thermostating means for thermostating said body to a predetermined temperature, and a container-shaped jacket having an annular surface part defining an opening in said jacket, said body being mounted within said jacket in spaced heat-insulating relationship therewith, said surface part of said body substantially flushing with said annular surface part so that said annular surface part is in heat conductive relationship with said skin surface when said surface part of said body is in heat conductive relationship with the said skin surface, said jacket including second thermostating means for thermostating said jacket to such a temperature that the heat transport or heat flux from said body is substantially unidirectional, and the spaced heat-insulating relationship between said body and said jacket being such that said jacket establishes, in operation, a virtual heating jacket in the skin beneath said annular surface part so as to substantially direct all heat flow from said body to skin layers directly beneath said body.

Normally, the spaced heat-insulating relationship between said body and said jacket will be such that a substantially narrow space is defined between the outer periphery of said body and the adjacent inner surface of said jacket.

The jacket may, in principle, be heated to a temperature which is different from the temperature of the body, but it is generally preferred that the body and the jacket are adapted to be heated to the same temperature so as to obtain a zero heat flux between said two bodies.

Like in conventional electrode devices, the construction will normally be most suitable when the body has a substantially circular cylindrical shape, and the jacket will then suitably have a substantially annular wall part which is arranged coaxially relative to said body.

In order to obtain a high degree of sensitivity to and a fast response on perfusion changes, the thermostating time constant and the thermal time constant of the body should both be low. The thermostating time constant (related to the active, heating function of the body) should be as low as possible to permit the system to respond immediately to power transport from the body and maintain a constant temperature. The thermostating time constant is proportional to the heating resistance of the system constituted by the body and the heating means heating the body, and hence, the effective heat-conductive contact between the body and the heating means of the first thermostating means should be as high as possible. The thermal time constant (related to the passive, cooling function) should be low to permit the system to immediately sense a higher power consumption by the blood flow. The thermal time constant will be proportional to the thermal capacity of the body, which means that in order to obtain a low thermal capacity, the volume of the body should be as small as possible. At the same time, the heat-conductive contact area between the body and the skin surface should be as large as possible. All of these considerations are best fulfilled when the body is disc-shaped, allowing for an optimum heat-conductive contact between the heating means of the first thermostating means and for the smallest possible volume at a given heat-conductive skin contact area.

The first thermostating means may, in principle, comprise any combination of heating means and temperature sensing means which will be suitable for the purpose in view of the above considerations. One combination which has been found suitable in practice comprises an NTC-resistor and a heating resistor.

A compact and flat construction is obtainable when said first thermostating means is arranged on a first thick film substrate, and according to a preferred embodiment of the invention, the first thermostating means is constructed as thick film components on said first thick film substrate, the said thick film substrate preferably constituting said body.

In accordance with what has been stated above, this thick film substrate preferably has a plane or plane-convex shape. The thick film substrate will preferably have a thickness of about 0.2–1.5 mm, in particular about 0.3–0.8 mm. The diameter of the thick film substrate will normally be about 5–12 mm.

Thick film substrates which are especially suitable for the purpose of the invention because of their favourable combination of electrically insulating properties and specific heat capacity properties are thick film substrates made of alumina or beryllia.

The body may also be made using thin film technology. In such case, the sensor means and the thermostating means will normally be applied on the body by means of thin film technique. The thin film substrate may, e.g. be made of ceramic material such as alumina or beryllia, or of silicon. When using thin film technique for the body (and optionally for other components of the electrode device, in particular also for the jacket thermostating means), the dimensions of the body may be the same as stated above for thick film bodies, but the thin film technique also permits the use of thinner and/or smaller bodies, optionally with several sensors applied on one and the same body.

The thermostating time constant of the jacket should be as low as possible in order to permit the jacket to respond as fast as possible in thermostating. On the other hand, the thermal time constant of the jacket relating to passive cooling of the jacket should be as high as possible. Thus, the jacket may be made from any material showing suitable specific heat capacity for the purpose, e.g. a metal such as copper or silver. The thermostating means thermostating the jacket may suitably comprise similar components as the thermostating means thermostating the body. Thus, this second thermostating means suitably comprises an NTC-resistor and a heating resistor and is suitably arranged on a thick film substrate in heat-conductive connection with the jacket. Likewise, this second thermostating means is suitably constructed as thick film components on said thick film substrate, which suitably is a circular substrate that preferably has a plane or plane-convex shape. Also this substrate is preferably made of alumina or beryllia.

The thermal resistance between the body and the jacket should be sufficiently high to substantially eliminate thermal crosstalk between the body and the jacket. For this reason, the thermal resistance between said jacket and said body should preferably be at least one order of magnitude (power of 10) greater than the thermal resistance between the body and the capillary bed beneath the skin surface. At a circular body of alumina having a diameter of about 10.5 mm, this condition is fulfilled when the distance between the outer periphery of the body and the adjacent inner surface of the jacket is 2 mm and the distance between the upper surface of the body and the lower surface of the jacket is 3 mm.

The sensor means of the electrochemical measuring electrode device may be sensor means adapted for measurement of any blood parameter which can be measured by means of an electrochemical measuring electrode, e.g., pH or the partial pressure of a blood gas. The sensor means may be of any suitable type adapted to be included in the selected type of body. Examples of sensor means suitable for the present purpose appear, e.g., from Danish Patent Application No. 1650/81 and 1676/81, both in the name of Radiometer A/S and may, e.g., comprise sensor means for measuring the partial pressure of oxygen and/or carbon dioxide. When the sensor means are adapted for the measurement of the partial pressure of oxygen, they may suitably comprise a cathode of a noble metal capable of electrochemical reduction of oxygen, and an anode cooperating with said cathode and preferably being a silver anode.

In accordance with well-known principles for the construction of electrochemical measuring electrode devices, the device according to the invention will normally comprise a membrane and an electrolyte solution, said membrane being arranged adjacent to said surface part of said body so as to define a space wherein said electrolyte solution is confined.

The invention also relates to a method for transcutaneous measurement of a blood parameter, said method comprising: applying, to a skin surface of a person, an electrochemical measuring device comprising, in combination:

a body of a heat conductive material having a surface part adapted to be applied to the skin surface in heat-conductive relationship therewith, said body including sensor means adapted to respond, in operation, to said blood parameter, and first thermostating means, and a container-shaped jacket having an annular surface part defining an opening in said jacket, said body being mounted within said jacket in spaced heat-insulating relationship therewith, said surface part of said body substantially flushing with said annular surface part so that said annular surface part is in heat conductive relationship with said skin surface said jacket including second thermostating means, the spaced heat-insulating relationship between said body and said jacket being such that said jacket is capable of establishing a virtual heating jacket in the skin beneath said annular surface part so as to substantially direct all heat flow from said body to skin layers directly beneath said body.

thermostating said body to a predetermined temperature, thermostating said jacket to such a temperature that the heat transport or heat flux from said body is substantially unidirectional, and so that said jacket establishes a virtual heating jacket in the skin surrounding the periphery of said body so as to substantially direct all heat from said body to skin layers directly beneath said body, measuring the power supplied for thermostating said body to said predetermined temperature so as to estimate the blood flow in the skin with which the body is in heat conductive relationship, and measuring the blood parameter by means of said sensor means.

The measurement of the blood parameter in question is performed in the normal manner, suitable utilizing normal amplifying and/or recording means.

The body and the jacket are preferably thermostated to the same temperature to obtain a zero heat flux therebetween.

Conventionally, when measuring blood flow, the power eliminated by perfusion below the electrode may be expressed in the following manner:

$$Q = F \times C \times \Delta T \times A$$

wherein Q is the power being eliminated, F is the blood flow, C is the heat capacity of the blood, $\Delta T$ is the temperature increase of the blood, i.e. the difference between the capillary temperature, $T_C$, and the arterial temperature or the deep body temperature, $T_{DBT}$, and A is the area of the electrode device. This equation may be rearranged in the following manner:

$$F = Q/(C \times \Delta T \times A)$$

Q may be measured by measuring the power, $P_F$, before occlusion and by measuring the power, $P_U$, during occlusion, since $$Q = P_F - P_U.$$

A and C are constants, while $\Delta T$ may be measured. As mentioned above $$\Delta T = T_C - T_{DBT}$$

wherein $T_{DBT}$ may be estimated to approximately 34°–35° C. for an application site on the forearm or measured in a manner to be described below. $T_C$ may be calculated from the electrode temperature, $T_E$, from $P_F$, and the thermal resistance, R, from the electrode to the capillary tissue, since $$T_E - T_C = P_F \times R$$

which may be rearranged into $$T_C = T_E - P_F \times R.$$

$P_U$, i.e. the power generated during occlusion, may be determined during a single occlusion whereafter F may be registered continuously.

In case the deep body temperature is estimated, the above described method for measuring the blood flow, F, does, however, suffer from one major drawback since the measuring result may be affected by a change in deep body temperature, $T_{DBT}$. Such a change in deep body temperature may cause a major change of the power, Q, being eliminated and, consequently, a major change of the actual measuring result of the blood flow.

In an article by Fox and Sullivan in Journal of Physiology 1970, 212, pp 8–10, a method for measuring the deep body temperature, $T_{DBT}$, at skin surface is described. In an article by Kobayashi, Nemoto, Kaniya and Togawa in Medical and Biological Engineering, May 1976, pp. 361–363 a refinement of the above method for measuring the deep body temperature is described. A probe for carrying out the measuring method is also described and comprises two thermistors arranged on top of one another within a jacket-shaped encasing of heat-conductive material which is provided with heating means. The upper thermistor is arranged in heat-conductive contact with the jacket-shaped encasing which is adapted to be arranged in contact with the skin surface of a test person or a patient so that the lower thermistor arranged within the encasing is also arranged in contact with the skin surface. It is described that the deep body temperature, $T_{DBT}$, may be measured by controlling the heating of the encasing in such a manner that the temperature difference between the two thermistors becomes zero, i.e. so that the heat flow across the probe is zero. When the heat difference between the two thermistors is zero the temperature determined by any of said two thermistors equilibrates the deep body temperature, $T_{DBT}$.

In accordance with a particular feature of the present invention, the above mentioned deep body temperature measuring method may also be carried out by means of the electrochemical measuring electrode device according to the invention. By virtue of the special jacket configuration contacting the skin surface, the electrochemical measuring electrode device according to the invention is, in an alternative operational mode, adapted to carry out the said measuring method and, thus, in a very elegant way provide deep body temperature measuring results for the above described blood flow measuring method.

In this alternative operational mode, the jacket is thermostated to such a temperature that the temperature registered by the temperature sensing means of said first thermostating means and the temperature registered by the temperature sensing means of said second thermostating means are identical to one another and, consequently, identical to the deep body temperature, $T_{DBT}$.

BRIEF DESCRIPTION OF THE DRAWINGS

The present invention will now be further described with reference to the drawings, wherein FIG. 1 diagrammatically shows an elevational, sectional view of a first embodiment of an electrochemical measuring electrode device according to the invention located on a skin surface, FIG. 2 partly in elevational, sectional view a second embodiment of an electrochemical measuring electrode device according to the invention, FIG. 3 an exploded view of the second embodiment of the electrode device according to the invention shown in FIG. 2, FIG. 4 partly in elevational, sectional view a third embodiment of an electrochemical measuring electrode device according to the invention, FIG. 5 partly in elevational, sectional view a fourth embodiment of an electrochemical measuring electrode device according to the invention, FIG. 6 partly in elevational, sectional view a fifth embodiment of an electrochemical measuring electrode device according to the invention, FIG. 7 a detail of a further embodiment of an electrochemical measuring electrode device according to the invention, FIG. 8 a diagram showing the thermostating power generated in a conventional measuring electrode device and in an electrochemical measuring electrode device according to the invention, respectively, under various test conditions, FIG. 9 a diagram showing the temperature response, i.e. the temperature rise and temperature decay, of a conventional electrochemical measuring electrode device and of an electrochemical measuring electrode device according to the invention, FIG. 10 a diagram simultaneously showing a signal indicating the partial pressure of oxygen measured by means of an electrochemical measuring electrode device according to the invention and a signal indicating the power generated in said electrode device, FIG. 11 a diagram showing blood flow measuring results obtained by means of the electrochemical measuring electrode device according to the invention as compared to measuring results obtained simultaneously by counting the γ-emission from an Xe-133 dose, and FIG. 12 a diagram showing test results obtained by means of the electrochemical measuring electrode device according to the invention in an experiment simulating the measurement of the deep body temperature, $T_{DBT}$.

DESCRIPTION OF THE PREFERRED EMBODIMENTS

Figure 1:
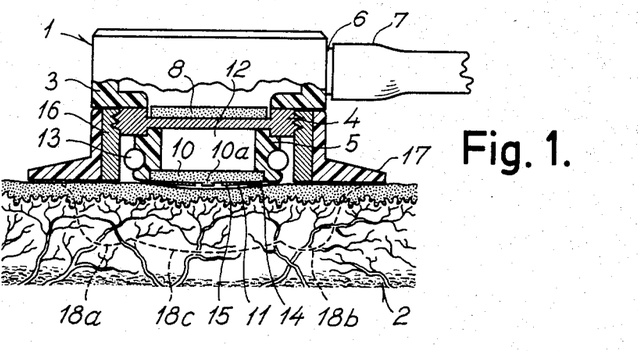

In FIG. 1 a first embodiment of an electrochemical measuring electrode device according to the invention is shown in which the main components of the electrode device are shown. The measuring electrode device designated 1 in its entirety is located at a skin surface shown schematically in FIG. 1 and designated 2. The electrode device 1 comprises an electrode housing 3 made of plastics, e.g. acrylonitrile-butadiene-styrene. The electrode housing 3 is connected to a metallic body 4 of material showing high heat conductivity, e.g. copper, the importance of which will be explained in greater detail below. Furthermore, the electrode device comprises an annular body 5 also made of plastics, e.g. acrylonitrile-butadiene-styrene. The electrode housing 3 is provided with a stub 6 adapted to cooperate with a multicore cable 7 the jacket of which is shown in FIG. 1 and which is adapted to connect the electrode device to external measuring equipment. On the metallic body 4 a thick film substrate 8, of e.g. alumina, is located in thermal conductive connection therewith. The substrate 8 is provided with thermostating means, i.e. temperature measuring means and temperature controlling means, e.g. an NTC-resistor and a heating resistor which may be constructed in thick film technique on the substrate or provided as discrete components as will be described in greater detail below. Furthermore, the electrode housing 3 is provided with a cover, not shown, opposite to the metallic body 4 and the thick film substrate 8. The interior space thus defined in the electrode housing 3 is filled up with an appropriate filling material or casting, e.g. an epoxy casting.

In a recess in the above mentioned annular body 5 a thick film substrate 10 of e.g. alumina is mounted which constitutes the sensor substrate in the inventive measuring electrode device in accordance with the principles described in Applicant's copending Danish patent applications No. 1650/81. The substrate 10 being a substantially circular substrate has a substantially plane upper surface as the substrate 8, which is a substantially circular substrate having two opposite plane surfaces, and a domed lower surface provided with a central protrusion 10a. Alternatively, the substrates 8 and 10 may be identical, i.e. of the above described type having a plane and a domed surface provided with a central protrusion. The inner space defined within the annular body 5 between the lower surface of the metallic body 4 and the upper surface of the substrate 10 is also filled with an appropriate filling material or casting, e.g. an epoxy casting. Before filling the interior spaces within the electrode housing 3 and within the annular body 5, the thermostating means located on the upper substrate 8 and the components of the sensor substrate 10 are connected through soldered joints to individual cores of the multicore cable 7.

The embodiment of the invention shown in FIG. 1 is a polarographic electrode device comprising an anode layer 11 and a cathode (not shown) arranged in a through-going passage in the central protrusion 10a of the sensor substrate 10 in a manner described in applicant's copending Danish patent application No. 1650/81. Furthermore, the anode layer 11 being a thick film silver layer is connected to a terminal field on the opposite side of the substrate 10 by means of a leading through connection in a manner also described in applicant's above mentioned Danish patent applications.

In an external, circumferential recess in the annular body 5, an O-ring 13 is located which secures a gas permeable and liquid impermeable membrane 14 relative to the lower domed surface of the sensor substrate 10. The membrane 14 may be made of e.g. polypropylene or tetrafluoroethylene. The above mentioned central protrusion 10a of the sensor substrate 10 provides, in combination with the membrane 14, an electrolyte reservoir 15 for an electrolyte solution of the electrochemical measuring electrode device.

The metallic body 4 is provided with external threads which are adapted to cooperate with corresponding internal threads of an annular metallic body 16, preferably also made of a material showing high heat conductivity, e.g. copper. Thus, the metallic body 16 is thermally connected to the substrate 8 through the metallic body 4. As will be appreciated, the two metallic bodies 4 and 16 constitute a metallic jacket enclosing the sensor substrate of the electrode device. The jacket and the sensor substrate are adapted to be thermostated by means of the thermostating means on the substrate 8 and the thermostating means on the substrate 10, respectively. As shown in FIG. 1 the annular metallic body 16 is mounted within an annular fixing ring 17 made of a material showing excellent thermal insulating qualities, e.g. plastics including acrylonitrile-butadiene-styrene.

When in use, the sensor substrate 10 and thus the active surface of the electrochemical measuring electrode device and the jacket, i.e. the substrate 8 arranged in heat conductive connection with the metallic body 4 and the annular metallic body 16 are thermostatically heated to the same temperature, e.g. 45° C. The heating of the sensor substrate 10 and the jacket to the same temperature provides that there is substantially no net heat flow between the sensor substrate 10 and the jacket. Therefore, the heat flux from the sensor substrate 10 is unidirectional, i.e. has a downward direction to the skin surface below the active sensor surface of the sensor substrate. Apart from virtually insulating the sensor substrate 10 totally relative to the environment, the jacket also contributes to the heating of the skin surface below the electrode device in such a manner that any heat flux from the sensor substrate 10 to any part of the skin surface outside the jacket dimensions are virtually eliminated. Therefore, the jacket provides a virtual heat jacket in relation to the skin surface heated by the sensor substrate 10 so that the heat flow from the sensor substrate 10 apart from being unidirectional becomes virtually one-dimensional. This aspect is illustrated in FIG. 1 by a curve 18 (a, b, c) which is shown indicating an isoterm, i.e. a curve drawn through locations having identical temperature. As will be seen from FIG. 1, the width of the uniformly heated skin surface is largely increased as indicated by the outer branches of the curve (18a, 18b) relative to the situation in which only the sensor surface, i.e. the substrate 10, is thermostatically heated to a temperature above skin temperature (18c). This largely increased and uniformly heated skin surface, in which hyperemia is produced and which is obtained by means of the annular metallic body 16 in heat conductive connection with the substrate 8 being thermostatically heated to the same temperature as the sensor substrate 10, provides the excellent measuring results which may be obtained by means of the electrochemical measuring electrode device according to the invention as will be described in greater detail below.

Figure 2:
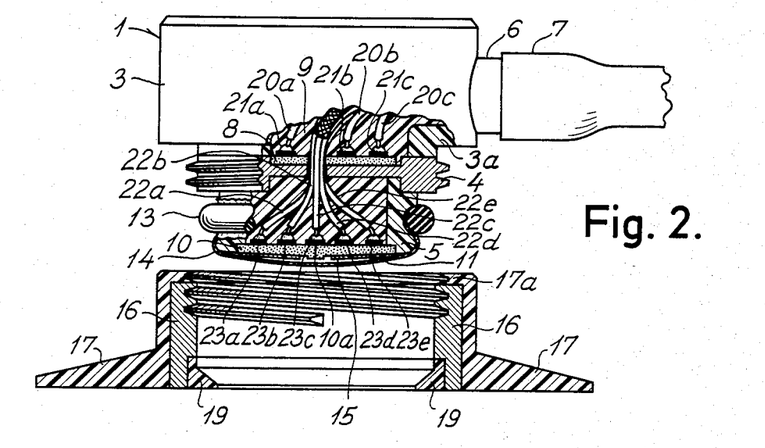

In FIG. 2, a second embodiment of the electrochemical measuring electrode device according to the invention is shown. The embodiment shown in FIG. 2 differs only slightly from the embodiment shown in FIG. 1 and therefore, identical reference numerals are being used for identical parts. Thus, the electrode housing 3 is provided with the protruding annular part designated 3a, and the annular fixing ring 17 is provided with a covering part 17a which covers the annular metallic body 16 which is mounted within the fixing ring 17. In the embodiment shown in FIG. 2, the said annular metallic body 16 is provided with an internal annular recess in which a thermally insulating ring body 19 is located, which is made of e.g. plastics including acrylonitrile-butadiene-styrene. In FIG. 2, several individual cores 20a, 20b, 20c, 22a, 22b, 22c, 22d and 22e of the multicore cable 7 are shown of which the cores 20a, 20b, and 20c are connected to the components on the substrate 8 through soldered joints 21a, 21b, and 21c, respectively. The cores 22a, 22b, 22c, 22d, and 22e are led through an aperture in the substrate 8 and an aperture in the metallic body 4 and connected to components on the substrate 10 through soldered joints 23a, 23b, 23c, 23d, and 23e, respectively.

Figures 3, 5, 7:
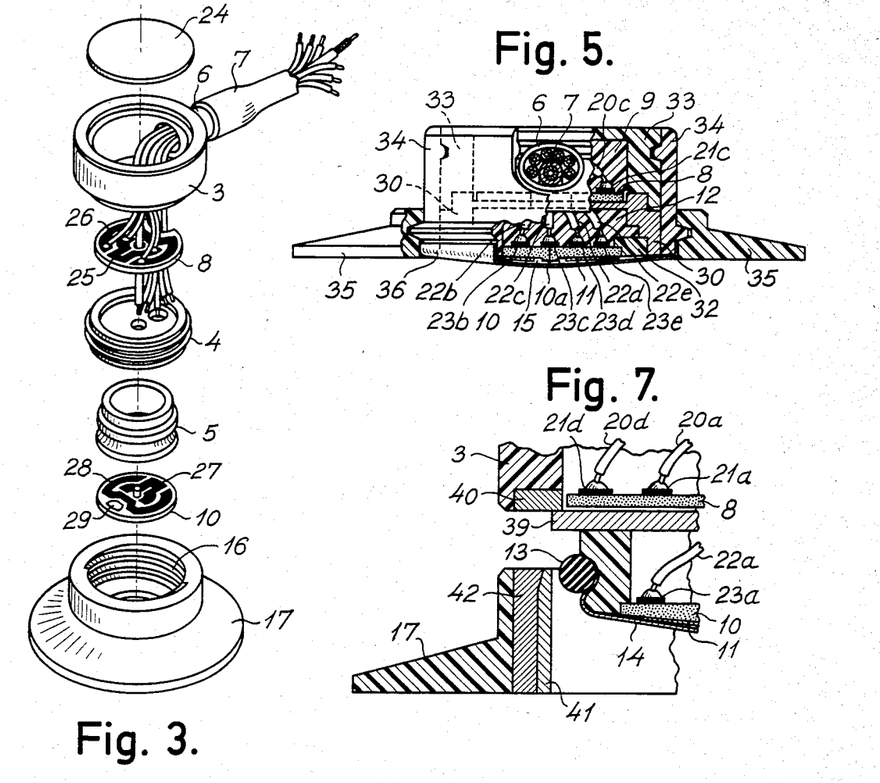

In FIG. 3, an exploded view of the above described second embodiment of the electrochemical measuring electrode device according to the invention is shown. Starting from above, a cover 24 is shown which has been mentioned above but which is not shown in FIGS. 1 or 2. Subsequently, the multicore cable 7, the electrode housing 3, the substrate 8, the metallic body 4, the annular body 5, the substrate 10, and the annular fixing ring 17 are shown. In FIG. 3, the substrates 8 and 10 are shown in greater detail compared to FIGS. 1 and 2. Thus, the thermostating means, i.e. the temperature measuring means and the temperature controlling means of the substrates 8 and 10, are shown. On the substrate 8, an NTC-resistor 25 and a heating resistor 26 are applied in thick film technique. Analogously, the substrate 10 is provided with an NTC-resistor 27 and a heating resistor 28 and, furthermore, a terminal field 29 for connection to an electrode of the sensor substrate of the electrochemical measuring electrode device. The construction and configuration of the electrode as well as the entire sensor substrate including thermostating means is disclosed in the above mentioned Danish patent application No. 1650/81.

Figure 4:
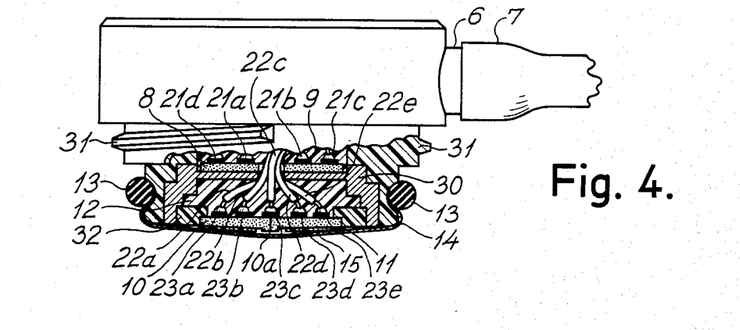

While the two above described embodiments of the electrochemical measuring electrode device according to the invention, i.e. the embodiments shown in FIG. 1 and in FIGS. 2 and 3, respectively, are adapted to be mounted within the annular fixing ring 17, the embodiment of the invention shown in FIG. 4 is adapted to be mounted within a conventional fixing ring. Therefore, the electrode housing 3, the metallic body 4, the annular body 5, the annular metallic body 16, as shown in FIGS. 1-3, are omitted in FIG. 4 and replaced by alternative components in order to permit mounting of the electrode device shown in FIG. 4 in the said conventional fixing ring. Instead of the metallic body 4 and the annular metallic body 16, constituting the jacket in the above described embodiments, the embodiment shown in FIG. 4 comprises a funnel-shaped metallic body or jacket 30 which is mounted within an electrode housing 31 which constitutes both the components 3 and 5 shown in FIGS. 1-3. Furthermore, the embodiment shown in FIG. 4 comprises an annular body 32 which is mounted within an internal recess in the funnel-shaped metallic body 30 and in an recess of which the sensor substrate 10 is mounted. Apart from the above mentioned cores 20a, 20b, 20c, 22a, 22b, 22c, 22d, and 22e and the above mentioned corresponding soldered joints 21a, 21b, 21c, 23a, 23b, 23c, 23d, and 23e, a fourth core 20d and a corresponding soldered joint 21d of a component on the substrate 8 are shown in FIG. 4.

In the embodiment of the invention shown in FIG. 4, the funnel-shaped metallic body 30 and the substrate 8 may be replaced by a single funnel-shaped body made of e.g. alumina which constitutes the jacket of the electrochemical measuring electrode device. Thus, the funnel-shaped body may be provided with a thick film component constructed on the substrate 8 in the embodiment shown in FIG. 4.

In FIG. 5 a fourth embodiment of an electrochemical measuring electrode device according to the invention is shown. Basically, the embodiment shown in FIG. 5 differs from the embodiment shown in FIG. 4 in that the total size or height of the electrode device including the fixing ring is reduced radically. This is obtained by integration of the electrode housing and the fixing ring.

Thus, the funnel-shaped metallic body or jacket 30 is mounted in a recess in a funnel-shaped body 33 also constituting the cover of the electrode device. The funnel-shaped body 33 may be made of e.g. acrylonitrile-butadiene-styrene. The funnel-shaped body 33 is provided with a circumferential groove which is adapted to cooperate, in a spring catch, with an internal annular protrusion of a ring 34 which is also provided with an external annular protrusion adapted to cooperate, in another spring catch, with a corresponding circumferential groove in a fixing ring 35 of conventional shape. The ring 34 and the fixing ring 35 are preferably made of plasticized polyvinyl chloride and polypropylene, respectively. In the funnel-shaped metallic body 30 the annular body 32, also shown in FIG. 4, is mounted. Within the above mentioned recess in the annular body 32, the sensor substrate 10 is mounted. The electrode device shown in FIG. 5 also comprises a membrane 36 which is secured to the ring 34 in an appropriate manner, e.g. by welding. In conjunction with the central protrusion 10a of the sensor substrate 10 and the anode layer 11, the membrane 36 provides the above described reservoir 15 for the electrolyte solution of the electrode device.

In the embodiment of the invention shown in FIG. 5, the stub 6 and the multicore cable 7 have an elliptical shape which also contributes to the overall reduction of the height of the electrode device.

Figure 6:
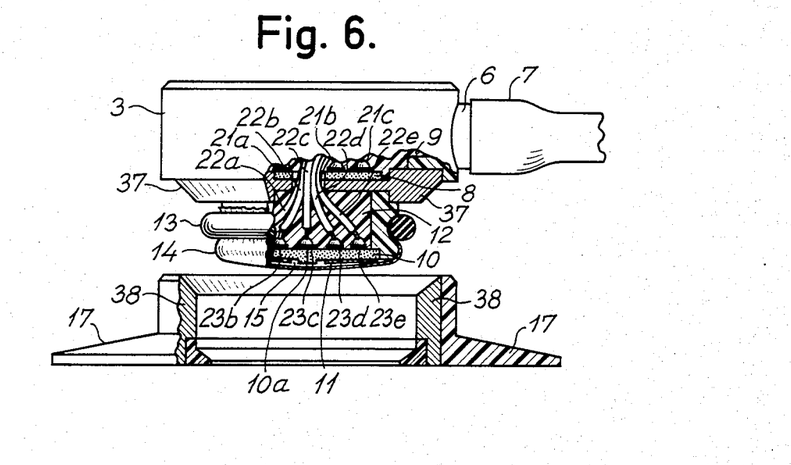

In FIGS. 6 and 7 two alternative embodiments of an electrochemical measuring electrode device according to the invention are shown. The embodiments of the invention hitherto described employ mechanical fixing of the electrode housing relative to the fixing ring. In the embodiments shown in FIGS. 6 and 7 magnetic fixing is employed. Thus, in the embodiment of the invention shown in FIG. 6, which differs from the embodiment of the invention shown in FIG. 2 in this aspect only, the metallic body 4 shown in FIG. 2 is replaced by a magnetic body 37. Similarly, in FIG. 6 the annular metallic body 16 shown in FIG. 2 is replaced by an annular magnetic body 38 showing high heat conductivity. As shown in FIG. 6 the magnetic body 37 has a frusto-conical shape and the annular magnetic body 38 has a conical upper surface adapted to fit and cooperate with the conical surface of the frusto-conical shape of the magnetic body 37. As will be appreciated, the magnetic body 37 and the annular magnetic body 38 are magnetized having opposite magnetic poles facing one another. The magnetic body 37 and the annular magnetic body 38 are preferably made of an AlNiCo material known as CROVAC ® or a CoRe-based material known as VACOMAX ®, and together constitute the jacket of the embodiment.

In an alternative embodiment of the invention shown in FIG. 7, the above described magnetic fixing means comprising the magnetic body 37 and the annular magnetic body 38 shown in FIG. 6 are replaced by a metallic plate 39 of a material showing high heat conductivity, such as copper, together with a magnetic ring 40, and an annular metallic body of a material showing high heat conductivity, such as copper, together with an annular magnetic body 42, respectively. The metallic plate 39 is mounted in thermal conductive connection and with the substrate 8 in the electrode housing 3 together with the magnetic ring 40. The annular metallic body 41 and the annular magnetic body 42 are mounted within the fixing ring 17. As will be appreciated, the magnetic ring 40 and the annular magnetic body 42 are magnetized having opposite magnetic poles facing one another. Furthermore, the magnetic ring 40 and the annular magnetic body 42 are preferably also made of CROVAC or VACOMAX and adapted to cooperate in such a manner that the metallic plate 39 and the annular metallic body 41 are brought into thermal conductive connection when said magnetic means are fitted together so as to form the jacket.

FIGS. 8-12 illustrate results which may be obtained by means of the electrochemical measuring electrode device according to the invention.

Figure 8:
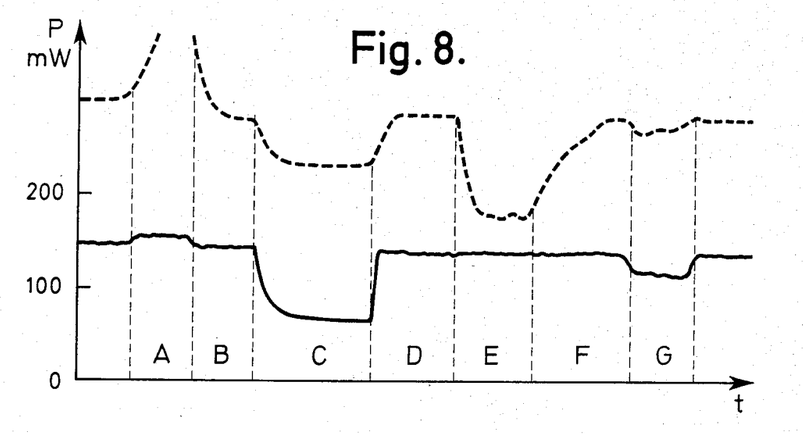

In FIG. 8, two curves are shown, one in dotted line and one in solid line showing results obtained by means of a conventional transcutaneous oxygen measuring electrode device and an electrochemical measuring electrode device of the kind shown in FIG. 2, respectively.

The conventional electrode device (Radiometer E 5240 from Radiometer A/S, Copenhagen) comprised a silver body of diameter about 6 mm thermostated by means of an NTC resistor and a zener diode. This conventional electrode contained no thermostated jacket around the body; the body was cast into a housing of ABS with a diameter of about 20 mm with epoxy casting between the body and the housing. Thus, the silver body was heat-insulated from the surroundings merely by means of the ABS housing and the epoxy casting. The electrode device of the kind shown in FIG. 2 had a sensor body 10 made of alumina and having a thickness of 0.635 mm and a diameter of 10.5 mm. The thermostating means comprised a discrete NTC resistor and a heating resistor applied on the substrate in thick film technique. The distance between the outer periphery of the sensor body and the adjacent inner surface of the jacket 16 was 2 mm, and the distance between the lower surface of the jacket and the upper surface of the body was 3 mm. The jacket consisted of copper, and the upper substrate 8 was of alumina. The outer diameter of the jacket was 16 mm. The space between the body 10 and the jacket was filled with epoxy casting material (Scotchcast ®250). The housing 3 and the annular fixing ring 17 were made of ABS.

The curves represent the power supplied to the body heating elements of the electrode devices to keep the body temperature at 45° C. under various tests conditions, plotted versus time. The abscissa is divided into sections A, B, C, D, E, F, and G, respectively, corresponding to the periods of time of the various test conditions mentioned above. After a period of time serving to reach steady state, the electrode devices are exposed to cold air, at A. After a period of time B serving stabilizing purposes, the blood flow of the test persons carrying the electrode devices is occluded, at C. After another period of stabilizing, D, the electrode devices are exposed to hot air, at E. After a period of stabilizing, F, the test person, at G, elevates his arm. Two main points should be noted. Firstly, the change of power at occlusion constitutes only 16.7% in the conventional electrochemical measuring electrode device while the change of power under the same test conditions constitutes 50% in the electrode device according to the invention. Secondly, the sensitivity to ambient changes is greatly reduced in the electrode device according to the invention.

In an alternative experiment, the annular metallic body 16 of the jacket was removed. Relative to the results described above, the power generated by the body of the electrode device, i.e. generated by the heating means of the sensor substrate 10, was increased by approximately 80% in steady state. In a further alternative experiment the jacket was disconnected and, consequently, the power generated by the body of the electrode device rose approximately 150% relative to the result described above, i.e. when employing the jacket according to the principles of the present invention.

Figure 9:
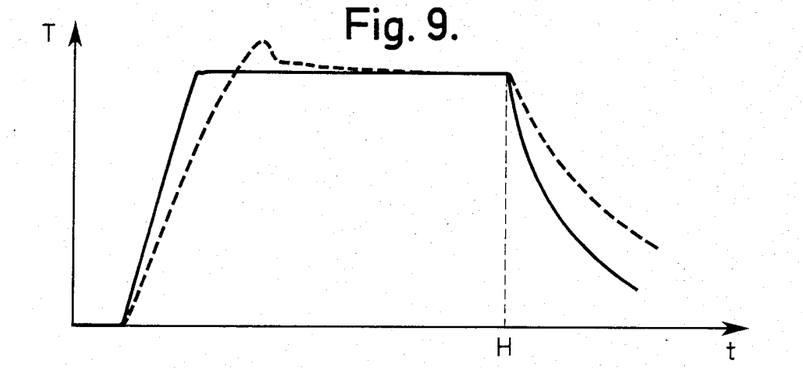

In FIG. 9, an essential advantage of a thick film body compared to a conventional body is illustrated. The conventional electrode device and the electrode device of the invention were the same as described in connection with FIG. 8. The two devices were arranged face to face at a distance of 3 cm from each other in still air at 25° C. 600 mW was supplied to the body heating means of each electrode device, the thermostating temperature of each body being preset at 43° C. The temperature response of each device was measured by means of its body thermostating temperature sensor. Two curves are shown, one in dotted line and one in solid line, showing the temperature response of the conventional electrode device and the electrode device according to the invention, respectively. From the figure it is seen that the initial response of the electrode device according to the invention is greatly improved, since the rise time is reduced, and the overshoot of the conventional electrode device is almost completely eliminated in the electrochemical measuring electrode device according to the invention. Furthermore, the decay time of the electrochemical measuring electrode device according to the invention is reduced compared to the conventional electrochemical measuring electrode device as indicated at H in FIG. 9. Therefore, the electrochemical measuring electrode device according to the invention with a thick film substrate constituting the body responds far more rapidly to temperature changes induced, and, of particular importance in the present context, will respond more rapidly to temperature changes induced in consequence of variations in the blood flow.

Figure 10:
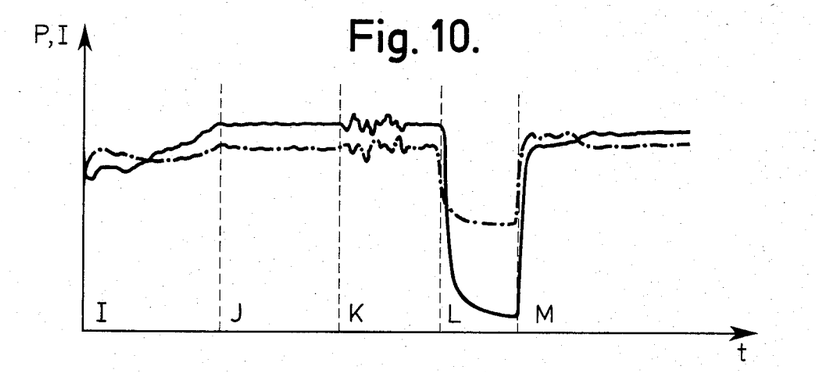

In FIG. 10 two curves are shown, one in dot-and-dash line, and one in solid line. The dot-and-dash lined curve and the solid line curve illustrate the power supplied to the electrochemical measuring electrode device according to the invention (the device described in connection with FIG. 8 above) when measuring on a forearm of a test person and a signal indicating the partial pressure of oxygen at the application site of said test person, respectively. After the period of stabilization, indicated as the period l, the curves reach steady state as indicated in the period J, whereupon a cuff is applied to the forearm of the test person during the period K. Thereafter, the blood flow is occluded and the curves show simultaneous decreases during the period L. The decrease in power generated in the electrode device make up approximately 50%. After the occlusion, the curves reach during the period M the same steady state values as in the period J.

Figure 11:
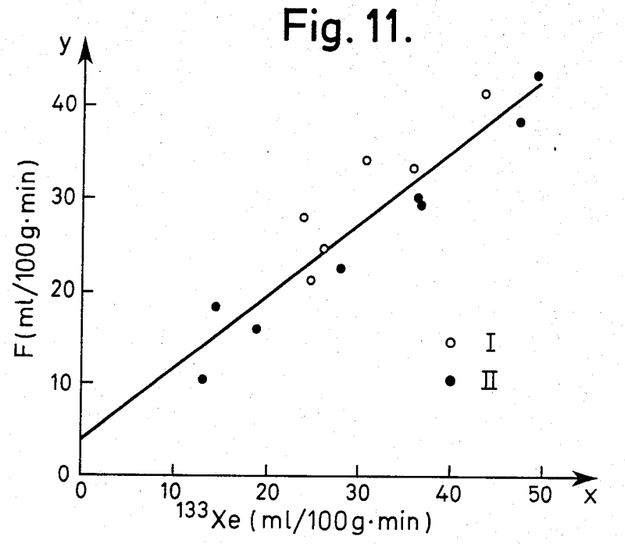

In FIG. 11 a diagram is shown illustrating blood flow measuring results obtained by means of the electrochemical measuring electrode device according to the invention and blood flow measuring results obtained simultaneously by a γ-emission counting method. By this γ-emission counting method, a dose of Xe-133 is implanted transcutaneously, and the depletion of Xe-133 is measured by counting the γ-emission decay by means of a scintillation-counter arranged above the implantion site. Measuring results obtained simultaneously by counting the γ-emission (X) and by means of the electrochemical measuring electrode device according to the invention in accordance with the blood flow measuring method described above (Y) are indicated by circles and dots referring to two different test persons. The measuring results obtained by means of the electrochemical electrode device according to the invention were corrected relative to drift caused by occlusion and recalculated into volume blood flow results by multiplying the measuring results obtained by a factor referring to skin thickness. Linear regression was carried out, and correlation coefficients were calculated. The line of regression, $Y=3.971+0.787\,X$, $r=0.932$, indicating an almost perfect agreement between the measuring results obtained in accordance with the two different measuring methods is shown in FIG. 11.

Figure 12:
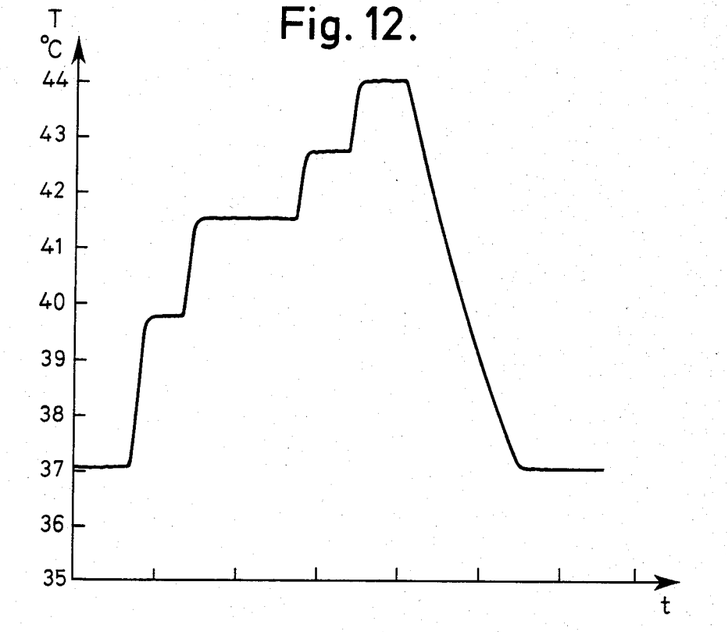

In FIG. 12 a diagram is shown illustrating measuring results obtained in an experiment. In this experiment the electrochemical measuring electrode device according to the invention was adapted to measure deep body temperature simulated by a water bath having a predetermined temperature. The electrode device was arranged in a boat measuring 80×120 mm and made of polyvinylchloride, PVC, of a thickness of 1.3 mm. The polyvinylchloride layer of a thickness of 1.3 mm corresponds thermally to a skin thickness of approximately 3 mm. When measuring deep body temperature simulated in the water bath, the annular jacket is heated in such a manner controlled by the temperature sensing means of the electrode body that any temperature difference between the temperature measured by the temperature sensing means of the body and the temperature measured by the temperature sensing means of the jacket is substantially eliminated. The temperature of the water bath is altered and monitored by means of a calibrated thermometer. The temperature measured by the temperature sensing means of the electrode body was recorded and the measuring results thus obtained are indicated in the table below:

TABLE

| Water Temperature | Temperature measured by electrode device | Difference |
| --- | --- | --- |
| 35.72° C. | 35.7° C. | +0.02° C. |
| 37.12° C. | 37.05° C. | +0.07° C. |
| 38.02° C. | 37.9° C. | +0.12° C. |
| 39.82° C. | 39.8° C. | +0.02° C. |
| 41.62° C. | 41.55° C. | +0.07° C. |
| 42.87° C. | 42.75° C. | +0.12° C. |
| 44.17° C. | 44.05° C. | +0.12° C. |

From FIG. 12 it is seen that the electrode device when measuring the deep body temperature, $T_{DBT}$, provides exact measuring results within the temperature range 35°–45° C. The measuring results are not affected by the environmental temperature which was approximately 25° C.

We claim:

1. An electrochemical measuring electrode device for transcutaneous measurement of a blood parameter, said device comprising:

a body formed of a heat conductive material, said body including a surface part for application to a skin surface in heat conductive relationship therewith, sensor means for operatively responding to said blood parameter, and first thermostating means for thermostating said body to a predetermined temperature, said device further comprising, a container-shaped jacket formed of a heat conductive material, said jacket including an annular surface part defining an opening in said jacket, said body being mounted within said jacket in spaced heat-insulating relationship therewith, said surface part of said body being substantially flush with said annular surface part so that said annular surface part is in heat conductive relationship with the skin surface when said surface part of said body is in heat conductive relationship with the skin surface, said jacket further including second thermostating means for thermostating said jacket to such a temperature that the heat transport or heat flux from said body is substantially unidirectional, whereby the spaced heat-insulating relationship between said body and said jacket enables said jacket to establish, in operation, a virtual heating jacket in the skin beneath said annular surface part so as to substantially direct all heat flow from said body to skin layers directly beneath said body.

2. The electrochemical measuring electrode device according to claim 1, wherein said body has an outer periphery, said jacket has an inner surface adjacent to the outer periphery of said body, and the spaced heat-insulating relationship between said body and said jacket is such that a substantially narrow space is defined between the outer periphery of said body and the adjacent inner surface of said jacket.

3. The electrochemical measuring electrode device according to claim 1, wherein said first and second thermostating means comprise means for heating said body and said jacket to the same temperature so as to obtain a zero heat flux between said body and said jacket.

4. The electrochemical measuring electrode device according to claim 1, wherein said body has a substantially circular cylindrical shape.

5. The electrochemical measuring electrode device according to claim 4, wherein said jacket includes a substantially annular part which is arranged coaxially relative to said body.

6. The electrochemical measuring electrode device according to claim 1, wherein said body is disc-shaped.

7. The electrochemical measuring electrode device according to claim 1, wherein said first thermostating means comprises an NTC-resistor and a heating resistor.

8. The electrochemical measuring electrode device according to claim 1 and further including a first thick film substrate, said first thermostating means being arranged on said first thick film substrate.

9. The electrochemical measuring electrode device according to claim 8, wherein said first thermostating means comprises thick film components disposed on said first thick film substrate.

10. The electrochemical measuring electrode device according to claim 8, wherein said body is formed of said first thick film substrate.

11. The electrochemical measuring electrode device according to claim 8, wherein said first thick film substrate has a plane or plane-convex shape.

12. The electrochemical measuring electrode device according to claim 8, wherein said first thick film substrate has a thickness of about 0.2–1.5 mm, and preferably about 0.3–0.8 mm.

13. The electrochemical measuring electrode device according to claim 8, wherein said first thick film substrate has a diameter of about 5–12 mm.

14. The electrochemical measuring electrode device according to claim 8, wherein said first thick film substrate is made of alumina or beryllia.

15. The electrochemical measuring electrode device according to claim 1, wherein said second thermostating means comprises an NTC-resistor and a heating resistor.

16. The electrochemical measuring electrode device according to claim 8, wherein said jacket further includes a second thick film substrate and said second thermostating means is arranged on said second thick film substrate in heat-conductive connection with said jacket.

17. The electrochemical measuring electrode device according to claim 16, wherein said second thermostating means comprises thick film components disposed on said second thick film substrate.

18. The electrochemical measuring electrode device according to claim 16, wherein said second thick film substrate comprises a circular substrate.

19. The electrochemical measuring electrode device according to claim 16, wherein said second thick film substrate has a plane or plane-convex shape.

20. The electrochemical measuring electrode device according to claim 16, wherein said second thick film substrate is made of alumina or beryllia.

21. The electrochemical measuring electrode device according to claim 1, wherein the thermal resistance between said jacket and said body is at least one order of magnitude (power of 10) greater than the thermal resistance between the body and the capillary bed beneath the skin surface.

22. The electrochemical measuring electrode device according to claim 1, wherein said sensor means comprises measuring means for measuring the partial pressure of a blood gas.

23. The electrochemical measuring electrode device according to claim 22, wherein said measuring means comprises a cathode of a noble metal capable of electrochemical reduction of oxygen, and an anode cooperating with said cathode and preferably being a silver anode, for measuring the partial pressure of oxygen in blood.

24. The electrochemical measuring electrode device according to claim 1, further comprising a membrane and an electrolyte solution, said membrane being adjacent to said surface part of said body so as to define a space wherein said electrolyte solution is confined.

25. A method of transcutaneous measurement of a blood parameter, comprising:
applying, to a skin surface of a person, an electrochemical measuring device comprising, in combination:
a body formed of a heat conductive material, said body including a surface part for application to the skin surface in heat-conductive relationship therewith, sensor means for operatively responding to said blood parameter, and first thermostating means for thermostating said body to a predetermined temperature, and a container-shaped jacket formed of a heat-conductive material, said jacket including an annular surface part defining an opening in said jacket, said body being mounted within said jacket in spaced heat-insulating relationship therewith, said surface part of said body being substantially flush with said annular surface part so that said annular surface part is in heat conductive relationship with the skin surface when said surface part of said body is in heat conductive relationship with the skin surface, and said jacket further including second thermostating means for thermostating said jacket to a particular temperature,
thermostating said body to a predetermined temperature with said first thermostating means,
thermostating said jacket to such a temperature with said second thermostating means that the heat transport or heat flux from said body is substantially unidirectional so that said jacket establishes a virtual heating jacket in the skin surrounding the periphery of said body to substantially direct all heat from said body to skin layers directly beneath said body, measuring the power supplied for thermostating said body to said predetermined temperature to enable estimation of the blood flow in the skin with which the body is in heat conductive relationship, and measuring the blood parameter by means of said sensor means.

26. The method according to claim 25, wherein said body and said jacket are thermostated to the same temperature.

27. The method according to claim 25, wherein said blood parameter is the partial pressure of a blood gas.

28. The method according to claim 25, wherein, in an alternative operational mode, said first thermostating means includes temperature sensing means for measuring the temperature of said first thermostating means, said second thermostating means includes temperature sensing means for measuring the temperature of said second thermostating means, and said jacket is thermostated to such a temperature that the temperature registered by the temperature sensing means of said first thermostating means and the temperature registered by the temperature sensing means of said second thermostating means are identical to one another and, consequently, identical to the deep body temperature.

* * * * *